(12) United States Patent
Abecassis et al.

(10) Patent No.: US 8,367,715 B2
(45) Date of Patent: Feb. 5, 2013

(54) PYRAZOLE DERIVATIVES, PREPARATION THEREOF, AND THERAPEUTIC USE THEREOF

(75) Inventors: Pierre Yves Abecassis, Paris (FR); Pascal Desmazeau, Paris (FR); Michel Tabart, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/336,253

(22) Filed: Dec. 23, 2011

(65) Prior Publication Data

US 2012/0270918 A1    Oct. 25, 2012

Related U.S. Application Data

(63) Continuation of application No. PCT/FR2010/051394, filed on Jul. 2, 2010.

(30) Foreign Application Priority Data

Jul. 3, 2009 (FR) ...................................... 09 03270

(51) Int. Cl.
  *A61K 31/415* (2006.01)
  *C07D 231/10* (2006.01)
  *C07C 275/28* (2006.01)

(52) U.S. Cl. ........................ 514/406; 548/374.1; 564/55

(58) Field of Classification Search ................... 514/406; 548/374.1; 564/55
See application file for complete search history.

(56) References Cited

U.S. PATENT DOCUMENTS 6,331,541 B1 * 12/2001 Ko et al. .................... 514/237.2

* cited by examiner

*Primary Examiner* — Rebecca Anderson
*Assistant Examiner* — Samantha Shterengarts
(74) *Attorney, Agent, or Firm* — Brian R. Morrill

(57) ABSTRACT

The invention relates to pyrazole derivatives of general formula (I):

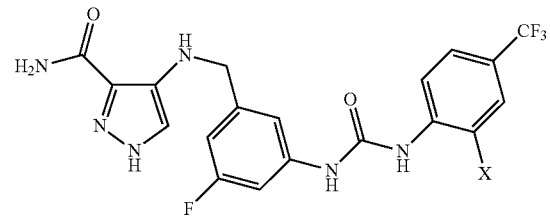

in which X represents chlorine or fluorine; to a process for preparing said derivatives, and to therapeutic uses of said derivatives.

9 Claims, No Drawings

PYRAZOLE DERIVATIVES, PREPARATION THEREOF, AND THERAPEUTIC USE THEREOF

The present invention relates to pyrazole derivatives, to the preparation thereof and to the therapeutic use thereof.

More particularly, and according to a first aspect, the invention relates to novel specific substituted pyrazoles with anticancer activity, via modulation of the activity of proteins, in particular kinases.

Protein kinases are a family of enzymes that catalyse the phosphorylation of hydroxyl groups of specific residues of proteins such as tyrosine, serine or threonine residues. Such phosphorylations can largely modify the function of proteins; thus, protein kinases play an important role in regulating a wide variety of cell processes, especially including metabolism, cell proliferation, cell differentiation, cell migration or cell survival. Among the various cellular functions in which the activity of a protein kinase is involved, certain processes represent attractive targets for treating cancer diseases and also other diseases.

Thus, one of the objects of the present invention is to propose compositions with anticancer activity, by acting in particular with respect to kinases. Among the kinases for which a modulation of activity is desired, mention may be made of KDR, Tie2, VEGFR-1 (FLT1), VEGFR-3 (FLT4), PDGFR and FGFR. The kinases KDR and/or Tie2 are preferred.

Compounds corresponding to the general formula (I) below are known from the patent application published under the number WO 08/065,282:

Formula (I)

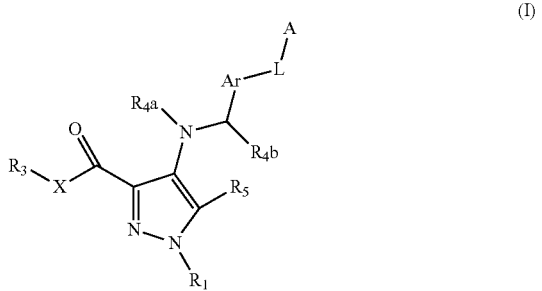

in which:
1) A and Ar are independently selected from the group constituted by: aryl, heteroaryl, substituted aryl, substituted heteroaryl;
2) L is selected from the group constituted by: NH—CO—NH and O—CO—NH;
3) $R_1$ is selected from the group constituted by: H, $R_6$, $COR_6$, $SO_2R_6$, in which $R_6$ is chosen from H, $OR_7$, $NR_8R_9$, alkyl, cycloalkyl, heterocyclyl, substituted heterocyclyl, aryl, substituted aryl, heteroaryl and substituted heteroaryl, in which $R_7$ is chosen from H, phenyl and alkyl, and in which $R_8$ and $R_9$ are independently selected from the group constituted by H, alkyl, cycloalkyl, heterocyclyl, substituted heterocyclyl, aryl, substituted aryl, heteroaryl and substituted heteroaryl, or alternatively $R_8$ and $R_9$ are linked together to form a saturated 5- to 8-membered ring containing from 0 to 3 heteroatoms chosen from O, S and N;
4) X is selected from the group constituted by: O and NH;
5) $R_3$ is selected from the group constituted by: H, alkyl, substituted alkyl, cycloalkyl, substituted cycloalkyl;
6) $R_4a$ is selected from the group constituted by: H and $(C_1-C_4)$alkyl;
7) $R_4b$ is selected from the group constituted by: H and $(C_1-C_4)$alkyl;
8) $R_5$ is selected from the group constituted by: H, halogen, $R_{10}$, CN, $O(R_{10})$, $OC(O)(R_{10})$, $OC(O)N(R_{10})(R_{11})$, $OS(O_2)(R_{10})$, $N(R_{10})(R_{11})$, $N=C(R_{10})(R_{11})$, $N(R_{10})C(O)(R_{11})$, $N(R_{10})C(O)O(R_{11})$, $N(R_{12})C(O)N(R_{10})(R_{11})$, $N(R_{12})C(S)N(R_{10})(R_{11})$, $N(R_{10})S(O_2)(R_{11})$, $C(O)(R_{10})$, $C(O)O(R_{10})$, $C(O)N(R_{10})(R_{11})$, $C(=N(R_{11}))(R_{10})$, $C(=N(OR_{11}))(R_{10})$, $S(R_{10})$, $S(O)(R_{10})$, $S(O_2)(R_{10})$, $S(O_2)O(R_{10})$, $S(O_2)N(R_{10})(R_{11})$; in which each $R_{10}$, $R_{11}$, $R_{12}$ is independently selected from the group constituted by H, alkyl, alkylene, alkynyl, aryl, heteroaryl, cycloalkyl, heterocyclyl, substituted alkyl, substituted alkylene, substituted alkynyl, substituted aryl, substituted heteroaryl, substituted cycloalkyl, substituted heterocyclyl.

In this patent, preferably X is O, $R_3$ is methyl, $R_4a$ and $R_4b$ are H; L is NHCONH; A is phenyl; Ar is phenyl; but in this application no example describes the substitution of Ar and its effect on the pharmacokinetics.

One subject of the present invention are two compounds included in the preceding application that correspond to the formula (I):

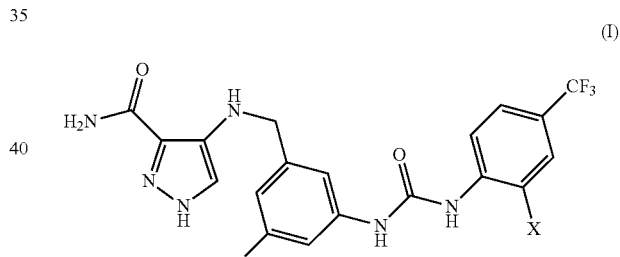

in which:
X represents Cl or F.

The compounds of formula (I) may exist in the form of bases or acid-addition salts. Such addition salts are part of the invention.

The compounds in their two tautomeric forms indicated below belong to the invention:

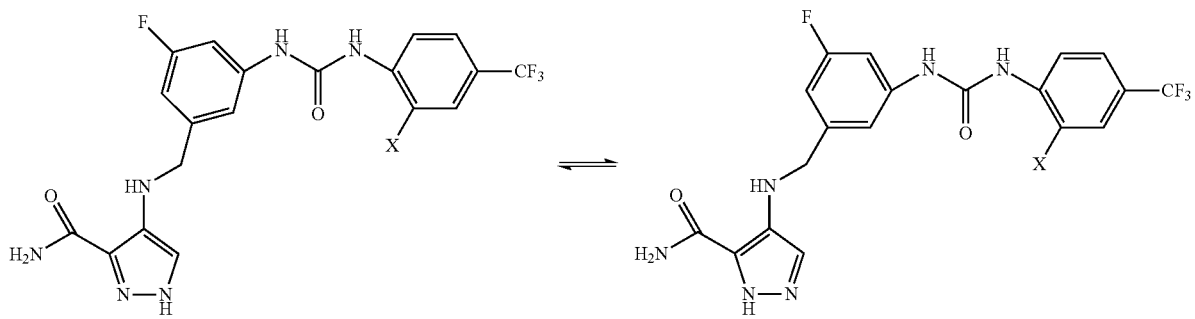

These salts may be prepared with pharmaceutically acceptable acids, but the salts of other acids that are of use, for example, for the purification or isolation of the compounds of formula (I) are also part of the invention. Among the salts that can be used, mention may especially be made of the hydrochloride.

The compounds of formula (I) may also exist in the form of hydrates or solvates, namely in the form of associations or combinations with one or more water molecules or with a solvent. Such hydrates and solvates are also part of the invention.

Among the compounds of formula (I) that are subjects of the invention, mention may especially be made of the following compounds:

4-{3-[3-(2-chloro-4-trifluoromethylphenyl)ureido]-5-fluorobenzylamino}-1H-pyrazole-3-carboxamide and its hydrochloride;

4-{3-[3-(2-fluoro-4-trifluoromethylphenyl)ureido]-5-fluorobenzylamino}-1H-pyrrazole-3-carboxamide and its hydrochloride.

In accordance with the invention, it is possible to prepare the compounds of general formula (I) according to the process that follows.

In the schemes which follow, the initial compounds and the reactants, when their method of preparation is not described, are commercially available or are described in the literature, or else may be prepared according to methods which are described therein or which are known to a person skilled in the art.

According to another of its aspects, another subject of the invention are the compounds of formulae:

in which X represents F or Cl.

These compounds are of use as synthetic intermediates of the compounds of formula (I).

The following examples describe the preparation of the compounds in accordance with the invention. These examples are not limiting and serve only to illustrate the present invention.

PROCESS FOR SYNTHESIS OF THE EXAMPLES

Synthesis of the Amino-Pyrazole Part

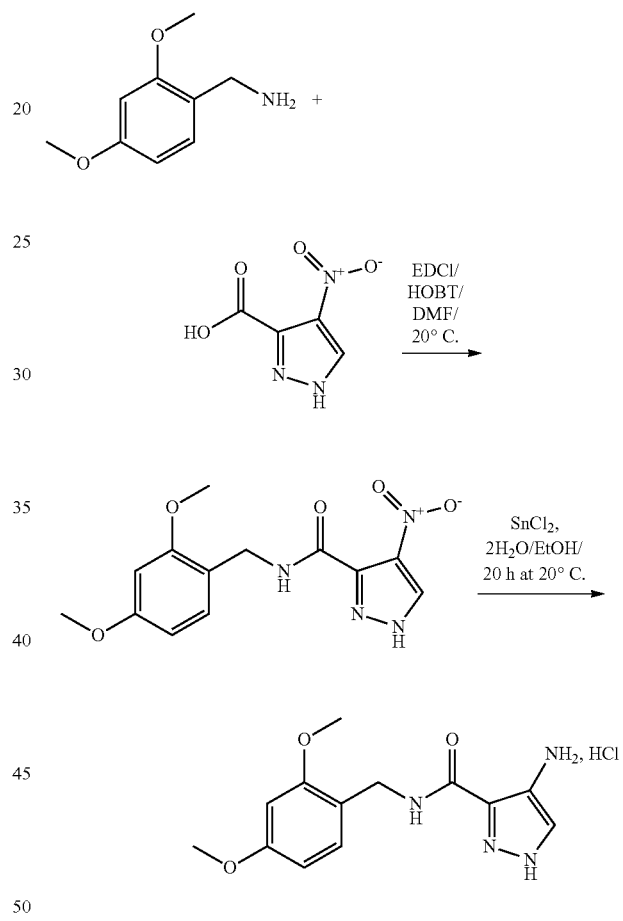

Synthesis of the Diaryl-Urea Part

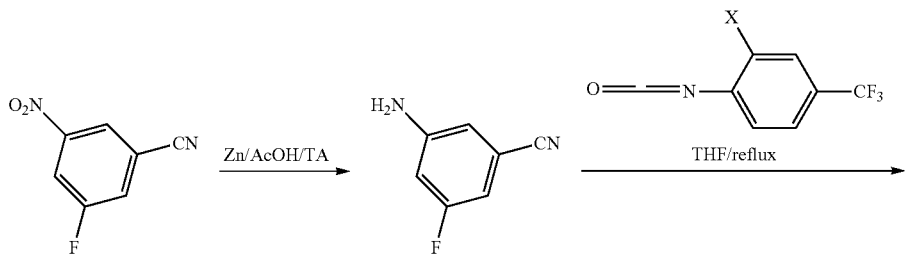

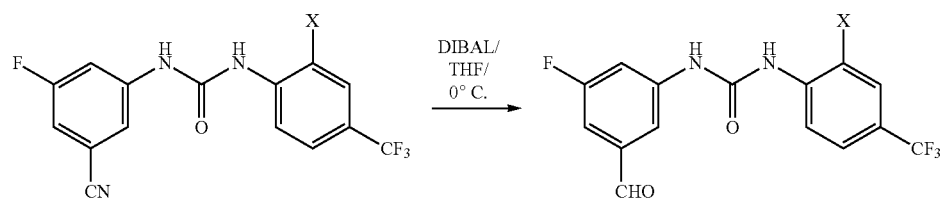
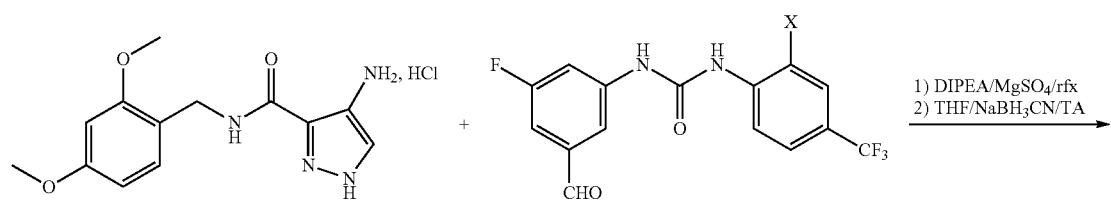
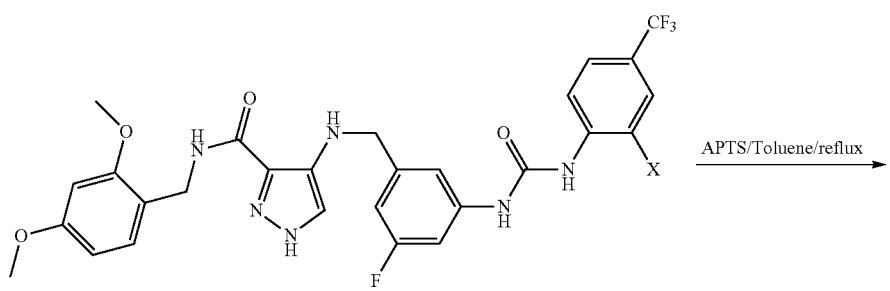
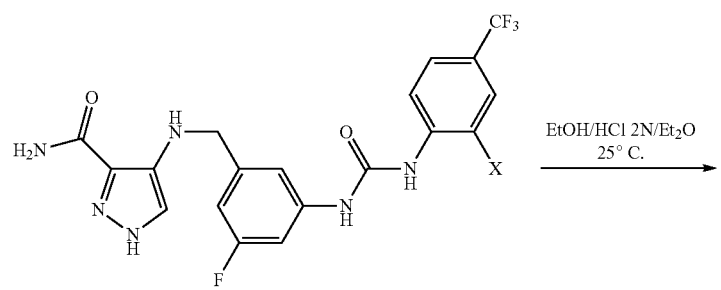
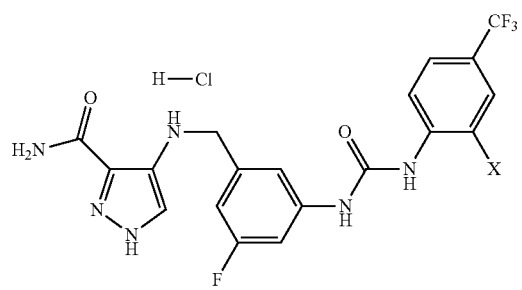

Example 1

4-{3-[3-(2-Chloro-4-trifluoromethylphenyl)ureido]-5-fluorobenzylamino}-1H-pyrazole-3-carboxamide hydrochloride

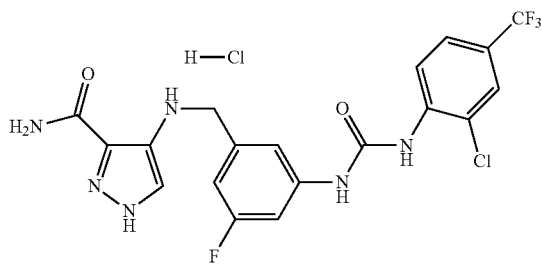

A suspension of 1.64 g (3.48 mmol) of 4-{3-[3-(2-chloro-4-trifluoromethylphenyl)ureido]-5-fluorobenzylamino}-1H-pyrazole-3-carboxamide in 50 ml of ethanol is stirred at ambient temperature under an argon atmosphere. Then 35 ml (35 mmol) of a solution of hydrochloric acid in diethyl ether (1 N) are added dropwise. The reaction medium becomes a clear solution. After stirring for 10 hours at ambient temperature, the solvents are evaporated using a rotary evaporator under reduced pressure. The residue obtained is stirred in 50 ml of diethyl ether for 30 minutes.

After filtration and drying in an oven, 1.8 g of 4-{3-[3-(2-chloro-4-trifluoromethylphenyl)ureido]-5-fluorobenzylamino}-1H-pyrazole-3-carboxamide hydrochloride; in the form of pale yellow crystals.

MS: Retention time Tr (min)=1.01; [M+H]$^+$ m/z=471; [M−H]$^-$ m/z=469

$^1$H NMR (400 MHz, DMSO-d) δ ppm 4.32 (s, 2H) 6.89 (broad d, J=9.6 Hz, 1H) 7.16 (broad s, 1H) 7.18-7.61 (m, 4H) 7.68 (broad d, J=8.9 Hz, 1H) 7.86 (broad s, 1H) 8.44 (d, J=8.9 Hz, 1H) 8.81 (broad m, 1H) 10.17 (broad m, 1H)

Melting point (Kofler)=177° C.

4-{3-[3-(2-Chloro-4-trifluoromethylphenyl)ureido]-5-fluorobenzylamino}-1H-pyrazole-3-carboxamide

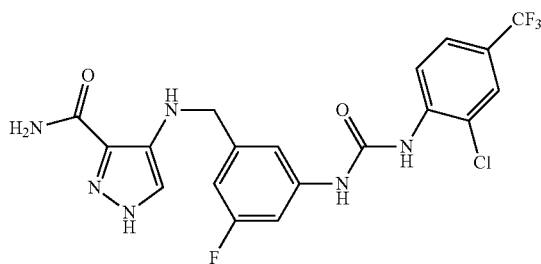

A solution of 5.9 g (9.5 mmol) of 4-{3-[3-(2-chloro-4-trifluoromethylphenyl)ureido]-5-fluorobenzylamino}-1H-pyrazole-3-(2,4-dimethoxybenzylamide) and 4.5 g (24 mmol) of para-toluenesulphonic acid in 400 ml of toluene is heated at reflux for 2 hours. After settling, the toluene solution is separated from a yellow gum. The gum is diluted in 150 ml of methanol and 500 ml of ethyl acetate. Then 500 ml of water are added. Next the solution is cooled, then basified with 100 ml of an aqueous solution of potassium hydroxide (10 N).

After settling, the aqueous phase is extracted with a solution of 400 ml of ethyl acetate and 100 ml of methanol. The organic phases are recombined and washed with 100 ml of a saturated sodium chloride solution, dried over magnesium sulphate and concentrated under reduced pressure to give a pale yellow solid which is purified over 200 g of silica, eluted with an 80/10/10 (by volume) solution of dichloromethane/methanol/acetonitrile: 1.77 g of 4-{3-[3-(2-chloro-4-trifluoromethylphenyl)ureido]-5-fluorobenzylamino}-1H-pyrazole-3-carboxamide are obtained in the form of a white solid.

MS: Retention time Tr (min)=4.29; [M+H]$^+$ m/z=471; [M−H]$^-$ m/z=469

$^1$H NMR (400 MHz, DMSO-d) δ ppm 4.19 (d, J=6.7 Hz, 2H) 5.74 (broad m, 1H) 6.80 (broad d, J=9.6 Hz, 1H) 6.95-7.11 (m, 3H) 7.24 (broad unresolved m, 1H) 7.42 (dt, J=11.3, 2.3 Hz, 1H) 7.67 (broad d, J=8.9 Hz, 1H) 7.86 (broad s, 1H) 8.44 (d, J=8.9 Hz, 1H) 8.70 (broad s 1H) 9.92 (broad s, 1H) 12.57 (broad s, 1H)

Melting point (Kofler): 220° C.

4-{3-[3-(2-Chloro-4-trifluoromethylphenyl)ureido]-5-fluorobenzylamino}-1H-pyrazole-3-(2,4-dimethoxybenzylamide)

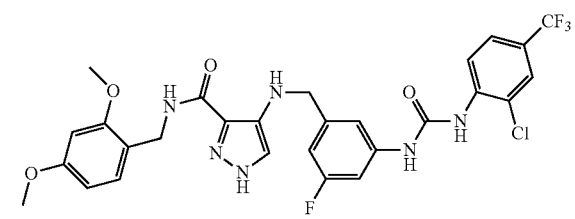 [SMILES: COc1ccc(CNC(=O)c2n[nH]cc2NCc2cc(F)cc(NC(=O)Nc3ccc(C(F)(F)F)cc3Cl)c2)c(OC)c1]

A solution of 10 g (32 mmol) of 4-amino-1H-pyrazole-3-(2,4-dimethoxybenzylamide) hydrochloride and 5.9 ml (35.2 mmol) of diisopropylethylamine in 300 ml of tetrahydrofuran is stirred at ambient temperature under an argon atmosphere. 3.85 g (35 mmol) of magnesium sulphate and 12.70 g (35.2 mmol) of 1-(2-chloro-4-trifluoromethylphenyl)-3-(3-fluoro-5-formylphenyl)urea are added. The reaction mixture is then heated at reflux for 14 hours. The mixture is then cooled to 25° C., then 10.08 g (160 mmol) of sodium cyanoborohydride are slowly added. After stirring for 12 hours at ambient temperature, the mixture is concentrated to dryness using a rotary evaporator. The gum obtained is stirred with 300 ml of water and 500 ml of an aqueous solution of sodium hydroxide (1N). This suspension is stirred for 30 minutes with 1 L of dichloromethane. After filtration through No. 3 sintered glass, the solid obtained is rinsed with 2×500 ml of water then dried in an oven under vacuum at 40° C. The solid is then recrystallized in 800 ml of methanol, at high temperature, to give 8.3 g of 4-{3-[3-(2-chloro-4-trifluoromethylphenyl)ureido]-5-fluorobenzylamino}-1H-pyrazole-3-(2,4-dimethoxybenzylamide) in the form of a white powder.

MS: Retention time Tr (min)=4.97; [M+H]$^+$ m/z=621; [M−H]$^-$ m/z=619

$^1$H NMR (400 MHz, DMSO-d) δ ppm 3.73 (s, 3H) 3.81 (s, 3H) 4.19 (d, J=6.7 Hz, 2H) 4.33 (d, J=6.7 Hz, 2H) 5.71 (broad t, J=6.7 Hz, 1H) 6.46 (dd, J=8.3, 2.3 Hz, 1H) 6.55 (d, J=2.3 Hz, 1H) 6.80 (broad d, J=9.6 Hz, 1H) 7.04 (broad s, 1H) 7.08 (s, 1H) 7.10 (d, J=8.9 Hz, 1H) 7.43 (dt, J=11.4, 2.3 Hz, 1H) 7.67 (broad d, J=8.9 Hz, 1H) 7.86 (broad s, 1H) 7.94 (broad t, J=6.7 Hz, 1H) 8.45 (d, J=8.9 Hz, 1H) 8.62 (broad unresolved m, 1H) 9.79 (broad unresolved m, 1H) 12.60 (broad unresolved m, 1H)

Melting point (Kofler): 168° C.

1-(2-Chloro-4-trifluoromethylphenyl)-3-(3-fluoro-5-formylphenyl)urea

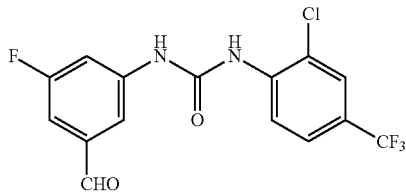 [SMILES: O=Cc1cc(F)cc(NC(=O)Nc2ccc(C(F)(F)F)cc2Cl)c1]

A solution of 33.15 g (92.68 mmol) of 1-(2-chloro-4-trifluoromethylphenyl)-3-(3-cyano-5-fluorophenyl)urea in 600 ml of tetrahydrofuran is stirred at −10° C. under an argon atmosphere. Next, 230 ml of a solution of diisobutylaluminium hydride at a concentration of 20% in toluene are added with a regular "dropwise" action. The reaction mixture is stirred at ambient temperature for 12 hours. Next, an additional 80 ml of diisobutylaluminium hydride are added at −10° C. After stirring for 14 hours at ambient temperature, the reaction medium is concentrated to dryness using a rotary evaporator in order to give a thick oil to which 500 g of ice and 100 ml of 100% acetic acid are slowly added, while stirring. The suspension obtained is filtered. The solid is then diluted in 2×800 ml of ethyl acetate and the organic solution is washed with 600 ml of a saturated sodium chloride solution, dried over magnesium sulphate, filtered, concentrated to dryness using a rotary evaporator and dried in an oven under vacuum at 40° C. in order to give 29.57 g of 1-(2-chloro-4-trifluoromethylphenyl)-3-(3-fluoro-5-formylphenyl)urea in the form of a pale yellow powder.

MS: Retention time Tr (min)=4.86; [M+H]⁺ m/z=361; [M−H]⁻ m/z=359

$^1$H NMR (400 MHz, DMSO-d) δ ppm 7.35 (ddd, J=8.4, 2.3, 1.8 Hz, 1H) 7.67-7.75 (m, 2H) 7.78 (t, J=1.8 Hz, 1H) 7.88 (d, J=1.8 Hz, 1H) 8.45 (d, J=8.8 Hz, 1H) 8.72 (broad s, 1H) 9.98 (d, J=1.8 Hz, 1H) 10.07 (broad s, 1H)

1-(2-Chloro-4-trifluoromethylphenyl)-3-(3-cyano-5-fluorophenyl)urea

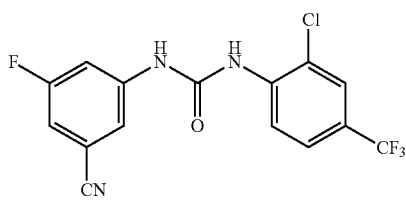

A solution of 15 g (110.2 mmol) of 5-fluoro-3-cyanoaniline in 150 ml of tetrahydrofuran is stirred at ambient temperature under an argon atmosphere. Next, 17.5 ml (121.22 mmol) of 2-chloro-4-trifluoromethylphenylisocyanate are added. The reaction medium is heated at reflux for 3 hours then concentrated to dryness using a rotary evaporator. The solid residue obtained is recrystallized at high temperature in 60 ml of ethyl acetate in order to give 33.25 g of 1-(2-chloro-4-trifluoromethylphenyl)-3-(3-cyano-5-fluorophenyl)urea in the form of a white solid.

MS: Retention time Tr (min)=4.97; [M+H]⁺: m/z=356
Melting point (Kofler): 286° C.
5-Fluoro-3-cyanoaniline is a commercial product.

4-Amino-1H-pyrazole-3-(2,4-dimethoxybenzylamide)hydrochloride

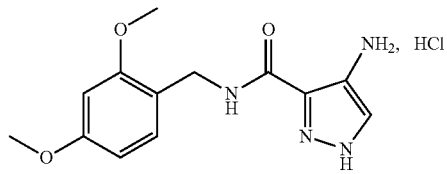 [SMILES: COc1ccc(CNC(=O)c2n[nH]cc2N)c(OC)c1 ; Cl]

A suspension of 6.12 g (20 mmol) of 4-nitro-1H-pyrazole-3-(2,4-dimethoxybenzylamide) in 340 ml of ethanol is stirred at ambient temperature. Next, 15.8 g (70 mmol) of tin chloride dihydrate are added over 5 minutes. The reaction mixture is stirred for 14 hours at ambient temperature, then concentrated to dryness using a rotary evaporator. The residue obtained is stirred with 330 ml of an aqueous solution saturated with sodiumhydrogen carbonate and 300 ml of dichloromethane. After settling, the organic phase is extracted with 2×150 ml of dichloromethane. The organic phases are recombined, washed with 150 ml of a saturated sodium chloride solution and dried over magnesium sulphate. After concentrating using a rotary evaporator, 4.57 g of 4-amino-1H-pyrazole-3-(2,4-dimethoxybenzylamide) hydrochloride are obtained in the form of a solid of purplish colour.

MS: EI: [M]⁺ m/z=276; base peak m/z=151

$^1$H NMR (400 MHz, DMSO-d) δ ppm 3.73 (s, 3H) 3.81 (s, 3H) 4.31 (d, J=6.2 Hz, 2H) 4.56 (broad unresolved m, 2H) 6.46 (dd, J=8.3, 2.9 Hz, 1H) 6.55 (d, J=2.9 Hz, 1H) 7.06-7.13 (m, 2H) 7.84 (t, J=6.2 Hz, 1H) 12.50 (broad unresolved m, 1H)

Melting point (Buchi): 186° C.

4-Nitro-1H-pyrazole-3-(2,4-dimethoxybenzylamide)

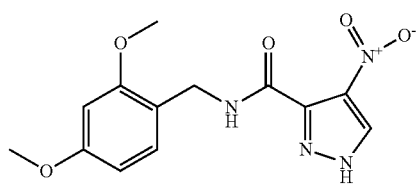 [SMILES: COc1ccc(CNC(=O)c2n[nH]cc2[N+](=O)[O-])c(OC)c1]

A solution of 14.65 g (76.4 mmol) of 1-(3-dimethylaminopropyl)-3-ethylcarbodiimide dihydrate and 10.32 g (76.4 mmol) of 1-hydroxybenzotriazole in 50 ml of dimethylformamide is stirred at ambient temperature. 11.7 g (70.03 mmol) of 2,4-dimethoxybenzylamine are added, then 10.2 g of 4-nitro-3-pyrazole carboxylic acid are added in small portions. After 16 hours of stirring at ambient temperature, the reaction medium is poured into 500 ml of water. The suspension is filtered, then washed with 2×250 ml of water. The solid obtained is dried in an oven under vacuum at 40° C. in order to give 18.58 g of 4-nitro-1H-pyrazole-3-(2,4-dimethoxybenzylamide) in the form of a white solid.

$^1$H NMR (400 MHz, DMSO-d) δ ppm 3.75 (s, 3H) 3.80 (s, 3H) 4.35 (d, J=5.9 Hz, 2H) 6.50 (dd, J=8.3, 2.4 Hz, 1H) 6.56 (d, J=2.4 Hz, 1H) 7.21 (d, J=8.3 Hz, 1H) 8.71 (broad s, 1 H) 8.88 (broad t, J=5.9 Hz, 1H) 14.13 (broad unresolved m, 1H)

MS (ES+/−) Retention time Tr (min)=3.23; [M+H]+ m/z=307; [M−H]− m/z=305

Melting point (Kofler): 192° C.

4-nitro-3-pyrazolecarboxylic acid is a commercial product.

Example 2

4-{3-[3-(2-Fluoro-4-trifluoromethylphenyl)ureido]-5-fluorobenzylamino}-1H-pyrazole-3-carboxamide hydrochloride

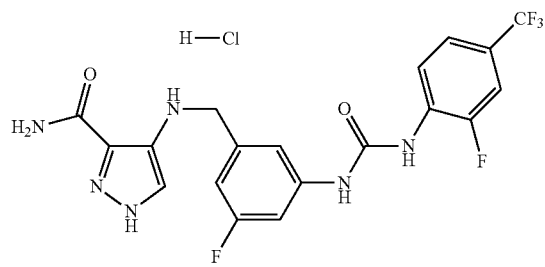 [SMILES: NC(=O)c1n[nH]cc1NCc1cc(F)cc(NC(=O)Nc2ccc(C(F)(F)F)cc2F)c1 ; Cl]

A suspension of 1.85 g (0.40 mmol) of 4-{3-[3-(2-fluoro-4-trifluoromethylphenyl)ureido]-5-fluorobenzylamino}-1H-pyrazole-3-carboxamide in 40 ml of ethanol is stirred at ambient temperature under an argon atmosphere. Then 20 ml (40 mmol) of a solution of hydrochloric acid in diethyl ether (1 N) are added dropwise. The reaction medium becomes a clear solution. After stirring for 12 hours at ambient temperature, the solvents are evaporated using a rotary evaporator under reduced pressure. The residue obtained is stirred in 200 ml of diethyl ether for 30 minutes.

After filtration and drying in an oven, 1.75 g of 4-{3-[3-(2-fluoro-4-trifluoromethylphenyl)ureido]-5-fluorobenzylamino}-1H-pyrazole-3-carboxamide hydrochloride; in the form of pale yellow crystals.

$^1$H NMR (400 MHz, DMSO-$d_6$) δ ppm 4.24 (s, 2H) 6.83 (d, J=9.0 Hz, 1H) 7.08 (s 1H) 7.18 (br. s., 1H) 7.23 (s, 1H) 7.35 (br. s., 2H) 7.42 (dt, J=11.3, 2.0 Hz, 1H) 7.54 (d, J=8.8 Hz, 1H) 7.69 (dd, J=11.2, 1.5 Hz, 1H) 8.41 (t, J=8.2 Hz, 1H) 8.99 (s, 1H) 9.54 (s, 1H)

MS: Retention time Tr (min)=0.97; [M+H]+ m/z=455

Melting point (Kofler): 184° C. (with decomposition)

4-{3-[3-(2-Fluoro-4-trifluoromethylphenyl)ureido]-5-fluorobenzylamino}-1H-pyrazole-3-carboxamide

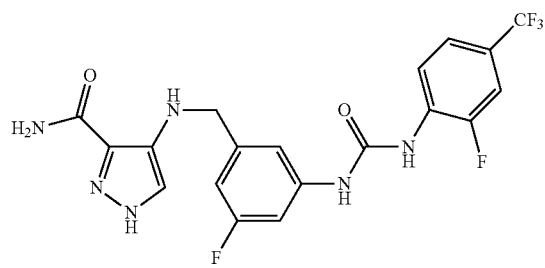

A solution of 22.3 g (36.89 mmol) of 4-{3-[3-(2-chloro-4-trifluoromethylphenyl)ureido]-5-fluorobenzylamino}-1H-pyrazole-3-(2,4-dimethoxybenzylamide) and 17.54 g (92.22 mmol) of para-toluenesulphonic acid in 600 ml of toluene is heated at reflux for 14 hours. After settling, the toluene solution is separated from a yellow gum. The gum is stirred for 2 hours in 280 ml of water and 100 ml of sodium hydroxide (10 N). The suspension is filtered. The solid obtained is rinsed with 3×350 ml of water then dried in order to give a cream solid which is purified over 350 g of silica, eluted with a 95/2.5/2.5 (by volume) solution of dichloromethane/methanol/acetonitrile: 3.85 g of 4-{3-[3-(2-fluoro-4-trifluoromethylphenyl)ureido]-5-fluorobenzylamino}-1H-pyrazole-3-carboxamide are obtained in the form of a white solid.

$^1$H NMR (400 MHz, DMSO-$d_6$) δ ppm 4.18 (d, J=5.9 Hz, 2H) 5.68-5.77 (m, 1H) 6.80 (d, J=8.8 Hz, 1H) 7.01-7.08 (br. s., 1H) 7.04 (s, 1H) 7.06 (s, 1H) 7.24 (br. s., 1H) 7.40 (dt, J=11.4, 2.0 Hz, 1H) 7.54 (d, J=8.3 Hz, 1H) 7.69 (d, J=11.5 Hz, 1H) 8.41 (t, J=8.4 Hz, 1H) 8.92 (br. s., 1H) 9.40 (br. s., 1H) 12.55 (br. s., 1H)

MS: Retention time Tr (min)=4.09; [M+H]+ m/z=455; [M−H]− m/z=453

Melting point (Kofler): 233° C.

4-{3-[3-(2-Fluoro-4-trifluoromethylphenyl)ureido]-5-fluorobenzylamino}-1H-pyrazole-3-(2,4-dimethoxybenzylamide)

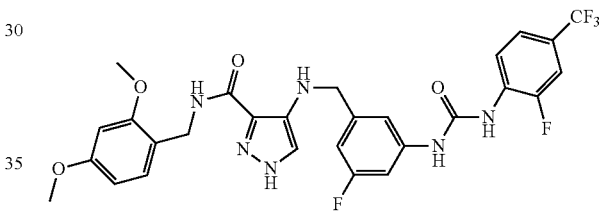

A solution of 11.40 g (36.45 mmol) of 4-amino-1H-pyrazole-3-(2,4-dimethoxybenzylamide) hydrochloride and of 6.65 ml (40.09 mmol) of diisopropylethylamine in 360 ml of tetrahydrofuran is stirred at ambient temperature under an argon atmosphere. 4.35 g (36.45 mmol) of magnesium sulphate and 13.80 g (35.2 mmol) of 1-(2-fluoro-4-trifluoromethylphenyl)-3-(3-fluoro-5-formylphenyl)urea are added. The reaction mixture is then heated at reflux for 14 hours. The mixture is then cooled to 25° C., then 11.46 g (182.25 mmol) of sodium cyanoborohydride are added slowly. After stirring for 72 hours at ambient temperature, the mixture is concentrated to dryness using a rotary evaporator. The gum obtained is stirred with 400 ml of water and 500 ml of a solution of sodium hydroxide (1N). This suspension is stirred for 1 hour, then filtered through No. 3 sintered glass, the solid obtained is rinsed with 3×500 ml of water, then dried in an oven under vacuum at 40° C. in order to give 22.45 g of 4-{3-[3-(2-fluoro-4-trifluoromethylphenyl)ureido]-5-fluorobenzylamino}-1H-pyrazole-3-(2,4-dimethoxybenzylamide) in the form of a pinkish solid.

$^1$H NMR (500 MHz, DMSO-$d_6$) δ ppm 3.73 (s, 3H) 3.81 (s, 3H) 4.18 (d, J=6.3 Hz, 2 H) 4.33 (s, 2H) −5.70 (t, J=6.2 Hz, 1H) 6.47 (d, J=8.2 Hz, 1H) 6.55 (s, 1H) 6.79 (d, J=9.1 Hz, 1H) 7.05 (s, 1H) 7.07-7.12 (m, 2H) 7.41 (d, J=11.3 Hz, 1H) 7.53 (d, J=8.2 Hz, 1H) 7.68 (d, J=11.3 Hz, 1H) 7.95 (br. s., 1H) − 8.40 (t, J=8.2 Hz, 1H) 9.25 (br. s., 2H) 12.52 (br. s., 1 H)

MS: Retention time Tr (min)=4.79; [M+H]⁺ m/z=605; [M−H]⁻ m/z=603

Melting point (Kofler): 152° C.

1-(2-Fluoro-4-trifluoromethylphenyl)-3-(3-fluoro-5-formylphenyl)urea

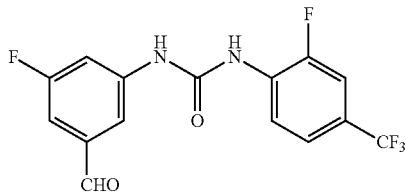 [SMILES: O=Cc1cc(F)cc(NC(=O)Nc2ccc(C(F)(F)F)cc2F)c1]

A solution of 11.90 g (34.87 mmol) of 1-(2-fluoro-4-trifluoromethylphenyl)-3-(3-cyano-5-fluorophenyl)urea in 150 ml of tetrahydrofuran is stirred at −2° C. under an argon atmosphere. Next, 86 ml of a solution of diisobutylaluminium hydride at a concentration of 20% in hexane are added with a regular "dropwise" action. The reaction mixture is stirred at ambient temperature for 12 hours. Next, an additional 60 ml of diisobutylaluminium hydride are added at −2° C. After stirring for 3 hours at ambient temperature, the reaction medium is concentrated to dryness using a rotary evaporator in order to give a thick oil to which 500 g of ice and 300 ml of 100% acetic acid are slowly added, while stirring. The suspension obtained is filtered. The solid obtained is washed with 4×150 ml of water, centrifuged and dried in an oven under vacuum at 40° C. in order to give 13.95 g of 1-(2-fluoro-4-trifluoromethylphenyl)-3-(3-fluoro-5-formylphenyl)urea in the form of a pale yellow solid.

¹H NMR (400 MHz, DMSO-d₆) δ ppm 7.33-7.38 (m, 1H) 7.57 (d, J=8.8 Hz, 1H) 7.69-7.75 (m, 2H) −7.79 (s, 1H) 8.41 (t, J=8.3 Hz, 1H) 9.05 (br. s., 1H) 9.65 (s, 1H) 9.98 (d, J=1.7 Hz, 1H)

MS: Retention time Tr (min)=4.62; [M+H]⁺ m/z=345; [M−H]⁻ m/z=343

Melting point (Kofler): 247° C.

1-(2-Fluoro-4-trifluoromethylphenyl)-3-(3-cyano-5-fluorophenyl)urea

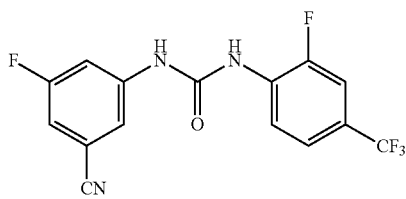 [SMILES: N#Cc1cc(F)cc(NC(=O)Nc2ccc(C(F)(F)F)cc2F)c1]

A solution of 6.15 g (45.18 mmol) of 5-fluoro-3-cyanoaniline in 90 ml of tetrahydrofuran is stirred at ambient temperature under an argon atmosphere. 4.3 ml (36.14 mmol) of diphosgene are added dropwise then 30 ml (135.54 mmol) of triethylamine. After refluxing in the reaction mixture for 3 hours, a solution of 7.10 g (39.64 mmol) of 4-amino-3-fluorotrifluoromethylbenzene in 10 ml of tetrahydrofuran is slowly added. The reflux is maintained for an additional 2 hours. The medium is then stirred into 100 ml of water, then extracted with 100 ml of ethyl acetate. The organic phase is washed with 100 ml of a saturated sodium chloride solution, dried over magnesium sulphate and concentrated to dryness using a rotary evaporator. The solid residue obtained is recrystallized at high temperature in 90 ml of acetonitrile in order to give 10.35 g of 1-(2-fluoro-4-trifluoromethylphenyl)-3-(3-cyano-5-fluorophenyl)urea in the form of a cream solid.

¹H NMR (400 MHz, DMSO-d₆) δ ppm 7.47 (d, J=8.3 Hz, 1H) 7.57 (d, J=8.6 Hz, 1H) 7.69 (s, 1H) 7.70-7.75 (m, 2H) 8.37 (t, J=8.4 Hz, 1H) 9.17 (br. s., 1H) 9.63 (br. s., 1H)

MS: Retention time Tr (min)=1.1; [M+H]⁺: m/z 341.

Melting point (Kofler): 253° C.

The products of the invention are useful as inhibitors of one or more reactions catalysed by a kinase. KDR and/or Tie2 are kinases for which the products of the invention will be particularly useful as inhibitors.

The reasons for which these kinases are chosen are given below:

KDR

KDR (Kinase insert Domain Receptor), also known as VEGF-R2 (Vascular Endothelial Growth Factor Receptor 2), is mainly expressed in endothelial cells. This receptor binds the proangiogenic growth factor VEGF, and thus serves as a transduction signal mediator via the activation of its intracellular kinase domain. The direct inhibition of the kinase activity of VEGF-R2 makes it possible to reduce the phenomenon of angiogenesis in the presence of exogenous VEGF (Vascular Endothelial Growth Factor) (Strawn et al., Cancer Research, 1996, vol. 56, p. 3540-3545). This process has especially been demonstrated using VEGF-R2 mutants (Millauer et al., Cancer Research, 1996, vol. 56, p. 1615-1620). The VEGF-R2 receptor appears to have no other function in adults than that associated with the angiogenic activity of VEGF. In addition to this central role in the dynamic angiogenic process, recent results suggest that the expression of VEGF contributes towards the survival of tumour cells after chemotherapy and radiotherapy, underlining the potential synergy of KDR inhibitors with other agents (Lee et al. Cancer Research, 2000, vol. 60, p. 5565-5570).

Tie2

Tie-2 (TEK) is a member of a family of tyrosine kinase receptors, which is specific to endothelial cells. Tie2 is the first receptor with tyrosine kinase activity for which both the agonist (angiopoietin 1 or Ang1), which stimulates the auto-phosphorylation of the receptor and cell signalling [S. Davis et al. (1996) Cell 87, 1161-1169], and the antagonist (angiopoietin 2 or Ang2) [P. C. Maisonpierre et al. (1997) Science 277, 55-60] are known. Angiopoietin 1 can have a synergistic effect with VEGF in the final stages of neoangiogenesis [Asahara T., Circ. Res. (1998) 233-240]. Knock-out experiments and transgenic manipulations of the expression of Tie2 or of Ang1 lead to animals that present vascularization defects [D. J. Dumont et al. (1994) Genes Dev. 8, 1897-1909 and C. Suri (1996) Cell 87, 1171-1180]. The binding of Ang1 to its receptor leads to autophosphorylation of the kinase domain of Tie2, which is essential for neovascularization and also for the recruitment and interaction of blood vessels with the pericytes and smooth muscle cells; these phenomena contribute towards the maturation and stability of the newly formed blood vessels [P. C. Maisonpierre et al. (1997) Science 277, 55-60]. Lin et al. (1997) J. Clin. Invest. 100, 8: 2072-2078 and Lin P. (1998) PNAS 95, 8829-8834 have shown an inhibition of tumour growth and vascularization, and also a reduction in lung metastases, during adenoviral infections or injections of the extracellular domain of Tie-2 (Tek) into models of melanoma and breast tumour xenografts.

For the reasons that follow, the Tie2 inhibitors may be used in situations in which neovascularization or angiogenesis takes place inappropriately, i.e. in cancers in general, but also in particular cancers such as Kaposi's sarcoma or infantile haemoangioma, rheumatoid arthritis, osteoarthritis and/or its associated pain, inflammatory diseases of the intestine such as haemorrhagic rectocolitis or Crohn's disease, eye pathologies such as age-related macular degeneration, diabetic retinopathies, chronic inflammation and psoriasis.

Angiogenesis is a process of generation of new blood capillaries from pre-existing blood vessels. Tumour angiogenesis (formation of new blood vessels), which is essential for tumour growth, is also one of the essential factors of metastasic dissemination (Oncogene. 2003 May 19; 22(20):3172-9; Nat. Med. 1995 January; 1(1):27-31).

This neovascularization is due to the migration and then the proliferation and differentiation of endothelial cells under the influence of angiogenic factors secreted by cancer cells and stromal cells (Recent Prog. Horm. Res. 2000; 55:15-35; 35-6).

The angiopoietin 1/Tie2 receptor system plays a predominant role in the maturation of blood vessels by allowing the recruitment of periendothelial cells to stabilize the vessels (Cell. 1996 Dec. 27; 87(7): 1161-9, Recent Prog. Horm. Res. 2004; 59:51-71). Thus, it has been shown that the administration of the soluble recombinant form of the extracellular domain of the Tie-2 receptor (exTek) inhibits tumour angiogenesis in models of murine tumours, and also metastatic growth (Proc. Natl. Acad. Sci. USA. 1998 Jul. 21; 95(15): 8829-34; Cancer Immunol Immunother. 2004 July; 53(7): 600-8). In endothelial cells in culture, stimulation of Tie-2 activates the PI3 kinase pathway, of p42/p44 pathways involved in cell proliferation and migration; of the synthesis of PAF (Cell Signal. 2006 Apr. 14; ahead of print), a pathway involved in pro-inflammatory activity. Stimulation of Tie2 stimulates the Akt pathway and inhibits apoptosis (Exp. Cell Res. 2004 Aug. 1; 298(1): 167-77), a transduction pathway known for its importance in cell survival.

The addition of exTek (soluble receptor of Tie2) inhibits the formation of pseudotubules of endothelial cells on Matrigel (Cancer Immunol Immunother. 2004 July; 53(7): 600-8). These studies indicate that the Tie-2/angiopoietin system is necessary during the first stages of formation of vascular buds in adult tissues and that one function of the Tie-2 receptor is to increase the survival of endothelial cells during the formation of blood vessels. Furthermore, angiopoietin-1 stimulates the proliferation of lymphatic endothelial cells and also lymphangiogenesis (development of new lymphatic vessels), a favoured access pathway for metastatic growth (Blood. 2005 Jun. 15; 105(12): 4649-56).

Among the enzymes that have a role in angiogenesis, mention may also be made of PDGFRβ (Univ. of Arizona, Molecular Cloning of the Human PDGFR-beta Promoter and Targeting the G-Quadruplex-Forming Region to Control Gene Expression; Biomedical Drug Discovery, Genomics/Gentics, Therapeutic), FGFR1 (Somaia Elbauomy Elsheikh, Andrew R Green,[1] Maryou B K Lambros, Nicholas C Turner, Matthew J Grainge,[3] Des Powe,[1] Ian O Ellis, and Jorge S Reis-Filho, FGFR1 amplification in breast carcinomas: a chromogenic in situ hybridization analysis; FLT1 (Shibuya M (2007), "Vascular endothelial growth factor receptor-1 (VEGFR-1/Flt-1): a dual regulator for angiogenesis", *Angiogenesis*, 9 (4): 225-30; discussion 231 and VEGFR3 (Tamela, T. et al., Blocking VEGFR-3 suppresses angiogenic sprouting and vascular network formation, Nature 454, 656-660 (20058).

Angiogenesis processes also play a predominant role in the progression of numerous solid tumours. Furthermore, it has been shown that the probability of onset of metastases increases very greatly as the vascularization of the primary tumour increases (Br. J. Cancer. 2002 May 20; 86(10): 1566-77).

The potential role of proangiogenic agents in leukaemias and lymphomas has also more recently been documented. Specifically, it has been reported in general that cell clones in these pathologies may be either naturally destroyed by the immune system, or revert to an angiogenic phenotype that favours their survival and then their proliferation. This change in phenotype is induced by an overexpression of angiogenic factors especially by the macrophages and/or mobilization of these factors from the extracellular matrix (Thomas D A, Giles F J, Cortes J, Albitar M, Kantarjian H M., *Acta Haematol.*, (2001), vol. 207, pp. 106-190).

There is a correlation between the angiogenesis process of bone marrow and "extramedullar diseases" in CML (chronic myelomonocytic leukaemia). Various studies demonstrate that the inhibition of angiogenesis might represent a treatment of choice in this pathology (Leuk. Res. 2006 January; 30(1): 54-9; Histol. Histopathol. 2004 October; 19(4): 1245-60). Furthermore, it is strongly suggested that activation of the Tie2/angiopoietin system is involved in the development of angiogenesis of bone marrow in the case of patients suffering from multiple myeloma (Blood, 2003 Jul. 15; 102(2): 638-45).

Determination of the Activity of the Compounds—Experimental Protocols

1. KDR

The inhibitory effect of the compounds is determined in an in vitro test of phosphorylation of substrate via a scintillation technique (96-well plate of basic Flash Plate type).

The cytoplasmic domain (residues 790 to 1356) of the human KDR enzyme was cloned in the form of a GST fusion in the pFastBac baculovirus expression vector. The protein was expressed in the SF21 cells, purified and activated by autophosphorylation. The substrate is composed of residues 658 to 850 of the PLCγ expressed and purified in the form of a GST fusion protein.

The KDR kinase activity is measured in the buffer 20 mM MOPS, 10 mM $MgCl_2$, 10 mM $MnCl_2$, 1 mM DTT, pH=7.4. The compounds are initially diluted in 100% DMSO, then prepared as a 10× solution in 30% DMSO/70% buffer. 10 µl of the 10× solution are deposited, then 70 µl of buffer containing 150 ng (1.6 pmol) of KDR enzyme at 4° C. The reaction is initiated by adding 20 µl of solution containing 2 µg (41 pmol) of PLCγ substrate, 0.5 µCi of $\gamma^{33}P[ATP]$ and 2 µM of cold ATP. The plate is agitated. After incubation for 30 minutes at 37° C., the incubation buffer is removed, and the wells are washed three times with 300 µl of PBS. The radioactivity in each well is measured using a Trilux-βWallac radioactivity counter.

The background noise is determined by measuring the radioactivity in four different wells containing ATP (radiolabeled and cold) and the substrate, in the absence of enzyme and of compound. The control activity is measured in four different wells containing all the reagents, but in the absence of compound.

The inhibition of the KDR activity with the compound of the invention is expressed as a percentage of inhibition of the control activity determined in the absence of compound.

2. Tie2

The inhibitory effect of the compounds is determined in an in vitro test of phosphorylation of substrate via a scintillation technique (96-well plate of basic Flash Plate type).

The coding sequence of human Tie2 corresponding to the amino acids of the intracellular domain 774-1124 was introduced into a pFastBacGT baculovirus expression vector in the form of a GST fusion protein. GST-Tie2 was purified and activated by autophosphorylation. The substrate is composed of residues 658 to 850 of the PLCγ expressed and purified in the form of a GST fusion protein.

The kinase activity of Tie2 is measured in a MOPS 20 mM pH 7.4 buffer, containing 10 mM MgCl$_2$, 10 mM MnCl$_2$ and 1 mM DTT. The compounds are initially diluted in 100% DMSO, then prepared as a 10× solution in 30% DMSO/70% buffer. 10 μl of the 10× solution are deposited, then 70 μl of buffer containing 100 ng (1.5 pmol) of Tie2 enzyme at 4° C. The reaction is initiated by adding 20 μl of solution containing 2 μg (41 pmol) of PLCγ substrate, 0.5 μCi of γ$^{33}$P[ATP] and 2 μM of cold ATP. The plate is agitated. After incubation for 30 minutes at 37° C., the incubation buffer is removed, and the wells are washed three times with 300 μl of PBS. The radioactivity in each well is measured using a Trilux-βWallac radioactivity counter.

The background noise is determined by measuring the radioactivity in four different wells containing ATP (radiolabeled and cold) and the substrate, in the absence of enzyme and of compound. The control activity is measured in four different wells containing all the reagents, but in the absence of compound.

The inhibition of the Tie2 activity is calculated and expressed as a percentage of inhibition relative to the control activity determined in the absence of compound.

3. Screening of Molecules by Measuring, by Radioactive Labeling, the FLT1 Kinase Phosphorylation Activity in the Presence of PFCγ Substrate The kinase activity of FLT1 is measured in the same way as the inhibition of Tie2 with a reaction mixture composed of 70 μl of kinase buffer containing 13 nM of FLT1 enzyme per well.

The inhibition of the FLT1 activity is calculated and expressed as percentage of inhibition relative to the control activity determined in the absence of compound.

The percentage of inhibition corresponding to each concentration of molecules is calculated thus:

% inhibition=(mean *CPM* of the control wells–*CPM* of each)

4. Screening of Molecules by Measuring, by Radioactive Labeling, the PDGFR Kinase Phosphorylation Activity in the Presence of PLCγ Substrate The test is carried out in a similar manner to that carried out with the FLT1 enzyme by using, instead of 13 nM of Flt1, 16 nM of PDGFR enzyme and mixed in the 96-well plates are 18 μl of GST-PDGFR enzyme at 4 mg/ml (for a purity of 80%) batch VLT802.

5. Screening of Molecules by Measuring, by Radioactive Labeling, the FGFR Kinase Phosphorylation Activity in the Presence of PLCγ Substrate The test is carried out in a similar manner to that carried out with the FLT1 enzyme by using, instead of 13 nM of Flt1, 27 nM of FGFR enzyme and mixed in the 96-well plates are 18 μl of GST-FGFR enzyme at 1.1 mg/ml (for a purity of 100%): (batch JCE3666).

Results:

The compounds of the examples of the invention have a concentration that inhibits 50% of the kinase activity which is generally between 0.1 nM and 2 μM on KDR and/or TIE2, preferably between 0.1 nM and 500 nM, and more preferably between 0.1 nM and 50 nM. The values from Table 1, below, are given by way of illustration.

| COMPOUNDS | KDR nM | Tie2 nM | PDGFRβ nM | FGFR1 nM | FLT1 nM | VEGFR3 nM |
|---|---|---|---|---|---|---|
| *[structure]* | 3 | 36 | 11 | 54 | 3 | 3 |
| *[structure]* | 2 | 39 | 20 | 92 | 1.3 | |

The compounds according to the invention were the subject of pharmacological tests enabling their hepatic clearance to be determined.

Evaluation of the intrinsic clearance of the compounds using human hepatocytes: experimental protocol.

NB: The in vitro test described below on human liver cells is used to predict an important pharmacokinetic parameter: the metabolization by the liver for a given compound when it is administered to man.

Culture Conditions:

Incubations of cryopreserved preparations of human hepatocytes (from IVT: IVT-TLN-180608 from In Vitro Technologies, inc. Baltimore, Md., USA) and fresh preparations of human hepatocytes (from Biopredic: HEP200239) were carried out in plates comprising 48 collagen-coated wells.

Experimental Conditions:

The kinetics were initiated by the addition, to the culture medium, of the compounds at a final concentration of 5 μM, in the absence or in the presence of 10 μM ketoconazole (CYP3A4 inhibitor). The incubation volume is 100 μl, the incubation time: 0-24 hours (standard kinetic points: 0-0.5-1-2-4-6-8-24 hours).

The kinetics were stopped by addition of acetonitrile/water, with corticosterone, as an internal standard. The cells were detached then lysed. The intracellular and extracellular media were recombined and frozen (−20° C.) in order to be stored until the LC-MS/MS analysis.

LC-MS/MS Analytical Method:

The combined extracellular and intracellular media were defrosted, submitted to ultrasound action, agitated with a vortex and centrifuged at 3000 g for 20 minutes. The supernatants were injected and analysed by LC-MS/MS.

Data Processing and "Classification"

The maximum initial in vitro rate was calculated for the specific metabolites of the P450 cytochromes and expressed in nmol/hour/million of cells.

$$V = [\text{concentration at } T(n) - \text{concentration at } T(n-1)]/[T(n)-T(n-1)]$$

The intrinsic clearance was determined and expressed in ml/hour/million of cells $$Cl_{int} = \text{dose}/AUC_{0-24\,h}$$

Dose=amount at $T(0)$(nmol/million of cells)

$AUC_{0-24\,h}$: calculated by WinNonlin, with a non-compartmental analysis modeling an intravenous injection of bolus type The classification of the intrinsic clearance was defined as follows:

$Cl_{int} < 0.040$ ml·h$^{-1}$·10$^{-6}$ cell: intermediate intrinsic clearance $0.040 < Cl_{int} < 0.120$ ml·h$^{-1}$·10$^{-6}$ cell: low intrinsic clearance $Cl_{int} > 0.040$ ml·h$^{-1}$·10$^{-6}$ cell: high intrinsic clearance Demographic information on the donor:

Preparations of cryopreserved human hepatocytes:

From IVT: ● IVT, TLN group: man, caucasian, 25 years old

Preparations of fresh human hepatocytes:

From Biopredic: ● HEP200239: woman, unknown, 58 years old

In this test, the intrinsic clearance value of the compound described in example 1 is 0.057 ml/hour/million of cells (value classified as intermediate with a low inter-individual variability).

The intrinsic clearance value of the compound described in example 2 is 0.055 ml/h/million of cells (value classified as intermediate with a low inter-individual variability).

Other tests consisting in measuring the in vivo activity of the compounds of the invention on colon tumours were carried out.

This activity of the compounds of the invention on colon tumours was studied on the B16 melanoma. In comparison, the product from example 19 of application WO 08/065,282 was tested.

The effectiveness of a product can be determined in vivo by various criteria, it is possible to determine it by the percentage of tumour inhibition % T/C, which represents the ratio between the average weight of the tumours of the treated group (T) and the average weight of the tumours of the control group (C) on day 12 or 13 of treatment. A product is considered to be active when the T/C ratio is less than 42% and a product has a high antitumour activity when the T/C is less than 10%. (Corbett T H et al., Cancer Research, 42, 1707-1715 (1982).

In order to demonstrate the effectiveness of a compound, it is also possible to determine the $\log_{10}$ cell kill, which is determined according to the following equation:

$$\log_{10} \text{cell kill} = T - C(\text{days})/3.32 \times T_d$$

in which T−C represents the delay in growth of the cells, which is the average time, in days, for the tumours of the treated group (T) and the tumours of the control group (C) to have reached a predetermined value (750 mg for example), and $T_d$ represents the time, in days, necessary for the volume of the tumour to double in the control animals [T. H. Corbett et al., Cancer, 40, 2660.2680 (1977); F. M. Schabel et al., Cancer Drug Development, Part B, Methods in Cancer Research, 17, 3-51, New York, Academic Press Inc. (1979)].

A product is considered to be active if $\log_{10}$ cell kill is greater than or equal to 0.7. A product is considered to be very active if $\log_{10}$ cell kill is greater than 2.8.

The effectiveness of the compounds on solid tumours can be determined experimentally in the following way:

The animals subjected to the experiment, generally C57BL/6 female mice, are grafted bilaterally, subcutaneously, with 30 to 60 mg of a B16 (reference of the tumour) human tumour fragment on day 0. The animals bearing the tumours are randomized before being subjected to the various treatments and controls. In the case of treatment of tumours of the present invention, the treatment was started at an early stage, 3 to 4 days after implantation. The animals which underwent the treatment with the compounds had a weight of around 20 g. Animals bearing tumours were also subjected to the same treatments with the excipient alone in order to be able to dissociate the toxic effect of the excipient from the actual effect of the chemotherapy on the tumour. The administrations of the compounds were carried out orally at the doses indicated in the tables and with the excipients indicated in the tables, according to a daily double administration. These administrations were carried out over 8 to 11 days, depending on the study, after implantation of the tumour.

The tumours are measured two or three times a week until the tumour reaches approximately 2 g or until the death of the animal if the latter occurs before the tumour reaches 2 g. The animals are autopsied at the time of sacrifice.

The antitumour activity is determined according to the various parameters recorded.

By way of examples, the following tables give the results obtained with the compounds of the invention used at their optimum dose.

The compounds according to the invention may therefore be used for the preparation of medicaments, in particular medicaments that inhibit angiogenesis.

Thus, according to another of its aspects, one subject of the invention is medicaments that comprise a compound of formula (I), or an addition salt of the latter with a pharmaceutically acceptable acid.

These medicaments find their therapeutic use especially in the treatment of cancerous tumours, especially solid tumours.

According to another of its aspects, the present invention relates to pharmaceutical compositions containing, as active principle, a compound according to the invention. These pharmaceutical compositions contain an effective dose of at least one compound according to the invention, or a pharmaceutically acceptable salt of said compound, and also at least one pharmaceutically acceptable excipient.

Said excipients are chosen according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the salt thereof, may be administered in a unit administration form, as a mixture with standard pharmaceutical excipients, to animals and to human beings for the treatment of the above disorders or diseases.

The appropriate unit administration forms include oral forms such as tablets, soft or hard gel capsules, powders, granules and oral solutions or suspensions, sublingual or buccal administration forms and transdermal, subcutaneous, intramuscular or intravenous administration forms.

By way of example, a unit administration form of a compound according to the invention in the form of a tablet may comprise the following components:

| | |
|---|---|
| Compound according to the invention | 50.0 mg |
| Mannitol | 223.75 mg |
| Croscaramellose sodium | 6.0 mg |
| Corn starch | 15.0 mg |
| Hydroxypropyl methyl cellulose | 2.25 mg |
| Magnesium stearate | 3.0 mg |

When given orally, the dose of active principle administered per day can reach . . . mg/kg, in one or more intakes.

There may be particular cases where higher or lower dosages are appropriate; such dosages do not depart from the context of the invention. Depending on the usual practice, the dosage appropriate for each patient is determined by the physician depending on the method of administration and the weight and response of said patient.

According to another of its aspects, the present invention also relates to a method for treating the pathologies indicated above, which comprises the administration, to a patient, of an effective dose of a compound according to the invention, or a pharmaceutically salt thereof Evaluation of Example 1 Against B16 Premature Murine Melanoma

| PO Compound (day of administration) | Dosage in mg/kg/ adm | Total dose in mg/kg | Death due to the product (day of death) | % BWC (day of low point) | Average weight of the tumour in mg on day 13 (range) | T/C in % day 13 | T − C in days 750 mg | Total log cell kill | Comments |
|---|---|---|---|---|---|---|---|---|---|
| Example 1 | 160.0 | 3178$^b$ | 0/5 | −2.3 (6) | 23 (0-89) | 2 | 6.8 | 2.6 | HDT active |
| Days 4-14 (2x/d)$^a$ | 99 | 1966$^b$ | 0/5 | −1.0 (5) | 72 (0-75) | 5 | 6.2 | 2.3 | Active |
| | 62 | 1232$^b$ | 0/5 | +1.8 (5) | 128 (75-273) | 10 | 6.2 | 2.3 | Active |
| Day 4-14 | 44 | 481$^b$ | 0/5 | +10.6 (15) | 686 (243-1418) | 51 | — | — | Inactive |
| Excipient PO 4-14 (2x/d) | | | 0/10 | +11.9 (15) | 1334 (496-1650$^c$) | | | | |

BCM-1948. Tumour doubling time = 0.8 day.
Formulation: Example 1 = 98% PEG200, 2% PS80.
Abbreviations used: BWC = body weight change, HNTD = highest nontoxic dose, HDT = highest dose tested.
$^a$Once a day for days 9 and 10.
$^b$The dose was reduced by accident by 7% on day 7.
$^c$Calculated on 9 mice due to one accidental death on day 8.

Evaluation of Example 2 Against B16 Premature Murine Melanoma

| PO Compound (day of administration) | Dosage in mg/kg/ adm | Total dose in mg/kg | Death due to the product (day of death) | % BWC (day of low point) | Average weight of the tumour in mg on day 11 (range) | T/C in % day 11 | T − C in days 750 mg | Total log cell kill | Comments |
|---|---|---|---|---|---|---|---|---|---|
| Example 2 | 160.0 | 2560.0 | 6/6 (10, 2d11, 13, 2d14) | −26.5 (13) | — | — | — | — | Toxic |
| Day 3-10 (2x/d) | 99.2 | 1587.2 | 0/6 | −8.1 (11) | 0 (0-14) | 0 | 5.4 | 1.8 | HNTD active |
| | 61.5 | 984 | 0/6 | +3.9 (11) | 46 (0-95) | 6 | 5.0 | 1.7 | Active |
| Day 3-10 | 44.0 | 352.0 | 0/6 | +6.6 (11) | 201 (23-822) | 27 | 3.0 | 1.0 | Active |
| Excipient PO 3-10 (2x/d) | | | 0/10 | +9.3 (11) | 736 (222-1328) | | | | |

BCM-1979. Tumour doubling time = 0.9 day. Average time for the tumours of the excipient group to reach 740 mg = 11.9 days.
Formulation: Example 2 = 20% labrasol, 5% solutol, 75% glucose, 5% water.
Abbreviations used: BWC = body weight change, HNTD = highest nontoxic dose, HDT = highest dose tested.

Evaluation of Example 19 from WO 08/065,282 Against B16 Premature Murine Melanoma

| Compound (day of administration) | Dosage in mg/kg/ adm | Total dose in mg/kg | Death due to the product (day of death) | % BWC (day of low point) | Average weight of the tumour in mg on day 12 (range) | T/C in % day 12 | T − C in days 750 mg | Total log cell kill | Comments |
|---|---|---|---|---|---|---|---|---|---|
| Example 18 from WO 08/065282 | 120.0 | 2554.3$^b$ | 0/7$^c$ | +8.3 (14) | 441 (270-594) | 29 | 4.2 | 1.2 | HDT active |
| p.o. 3-13 (2x/d)$^a$ | 74.4 | 1588.3$^b$ | 0/7$^c$ | +10.6 (14) | 459 (394-949) | 30 | 3.6 | 1.0 | Active |
| | 46.1 | 984.0$^b$ | 0/7 | −0.0 (4) | 849 (576-1093) | 56 | — | — | Inactive |

| Compound (day of administration) | Dosage in mg/kg/ adm | Total dose in mg/kg | Death due to the product (day of death) | % BWC (day of low point) | Average weight of the tumour in mg on day 12 (range) | T/C in % day 12 | T − C in days 750 mg | Total log cell kill | Comments |
|---|---|---|---|---|---|---|---|---|---|
| Excipient p.o. 3-13 (2x/d)[a] | — | | 0/10 | +18.3 (14) | 1522 (1000-1762) | | | | |

BCM-1755. Tumour doubling time = 1.1 day.
Formulation: Example 3 = 40% Captisol in water, pH = 3.
Treatment time: Example 3 = 11 days.
Abbreviations used: HDT = highest dose tested.
[a]On day 3, the mice were treated once per day.
[b]The total dose was reevaluated after the assaying of the mother solution by HPLC on days 3, 4 and 11 to 13.
[c]An accidental death, effectiveness calculated for 6 animals.

The invention claimed is:

1. A compound corresponding to the formula (I):

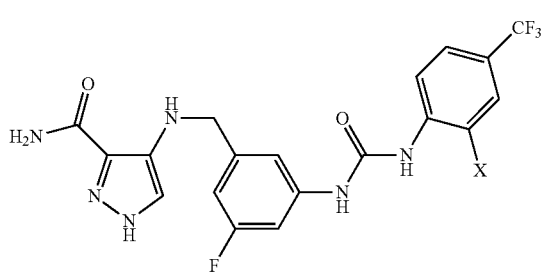

(I)

in which X represents chlorine or fluorine;
or a pharmaceutically acceptable salt thereof.

2. A compound according to claim 1, in which X represents chlorine;
or a pharmaceutically acceptable salt thereof.

3. A compound according to claim 1, in which X represents fluorine;
or a pharmaceutically acceptable salt thereof.

4. A process for preparing a compound according to claim 1, wherein said process comprises the steps of:
(a) reacting the compound:

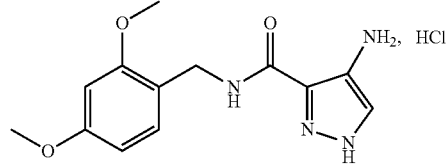 [SMILES: COc1ccc(CNC(=O)c2n[nH]cc2N)c(OC)c1 ; Cl]

with the compound:

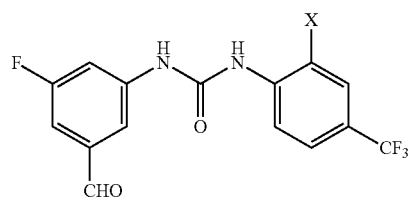

in which X represents chlorine or fluorine, wherein said reaction occurs in the presence of diisopropylethylamine in an inert medium; and (b) deprotecting the amine with para-toluenesulphonic acid.

5. The process according to claim 4, wherein said inert medium is an apolar aprotic medium.

6. The process according to claim 5, wherein said inert medium is tetrahydrofuran.

7. A compound of formula:

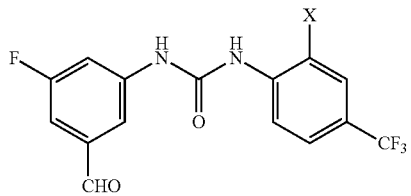

in which X represents chlorine or fluorine.

8. A compound of formula:

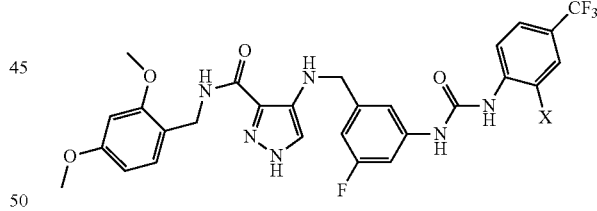

in which X represents chlorine or fluorine.

9. A pharmaceutical composition, comprising a compound according to claim 1, or a pharmaceutically acceptable salt thereof, and at least one pharmaceutically acceptable excipient.

* * * * *